(12) United States Patent
Heckerman et al.

(10) Patent No.: US 8,315,957 B2
(45) Date of Patent: Nov. 20, 2012

(54) PREDICTING PHENOTYPES USING A PROBABILISTIC PREDICTOR

(75) Inventors: David E. Heckerman, Santa Monica, CA (US); Carl Myers Kadie, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 551 days.

(21) Appl. No.: 12/551,606

(22) Filed: Sep. 1, 2009

(65) Prior Publication Data

US 2011/0055128 A1 Mar. 3, 2011

(51) Int. Cl.
  *G06F 15/18* (2006.01)
  *G06F 7/60* (2006.01)
  *G06F 7/00* (2006.01)
  *G06G 7/58* (2006.01)

(52) U.S. Cl. .................. 706/13; 703/2; 703/11; 707/705

(58) Field of Classification Search .................. None
  See application file for complete search history.

(56) References Cited

U.S. PATENT DOCUMENTS

| 7,660,709 B2 * | 2/2010 | Bugrim et al. .................... 703/2 |
| 2002/0098498 A1 | 7/2002 | Bader |
| 2003/0171876 A1 | 9/2003 | Markowitz et al. |
| 2006/0110751 A1 | 5/2006 | Salonen et al. |

OTHER PUBLICATIONS

Wang, et al., "A Bioinformatics Approach for the Phenotype Prediction of Nonsynonymous Single Nucleotide Polymorphisms in Human Cytochromes P450", Retrieved at <<http://dmd.aspetjournals.org/cgi/content/abstract/37/5/977>>, Feb. 9, 2009, p. 1.

Clement, et al., "Role of the DGAT Gene C79T Single-Nucleotide Polymorphism in French Obese Subjects", Retrieved at <<http://www.nature.com/oby/journal/v11/n10/full/oby2003160a.html>>, "Obesity Research (2003) 11, 1163-1167", Aug. 19, 2003, pp. 1-4.

Plenge, et al., "Identifying Relationships among Genomic Disease Regions: Predicting Genes at Pathogenic SNP Associations and Rare Deletions", Retrieved at << http://www.pubmedcentral.nih.gov/articlerender.fcgi?artid=2694358>>, Jun. 26, 2009, pp. 1-24.

Cox, et al., "Interpreting P Values in Pharmacogenetic Studies: A Call for Process and Perspective", Retrieved at <<http://jco.ascopubs.org/cgi/content/full/25/29/4513>>, "Journal of Clinical Oncology, vol. 25, No. 29 Oct. 10, 2007: pp. 4513-4515", pp. 1-5.

Lee, et al., "Predicting Unobserved Phenotypes for Complex Traits from Whole-Genome SNP Data", Retrieved at<<http://www.plosgenetics.org/article/info:doi/10.1371/journal.pgen.1000231>>, Jul. 22, 2009, pp. 1-19.

Subramanian, et al., "Gene set enrichment analysis: A knowledge-based approach for interpreting genome-wide expression profiles", PNAS, Oct. 25, 2005, vol. 102, No. 43, p. 6.

* cited by examiner

*Primary Examiner* — Alan Chen

(57) ABSTRACT

Aspects of the subject matter described herein relate to predicting phenotypes. In aspects, a probabilistic predictor is used to summarize a relationship between a set of biological predictors and a phenotype. The probabilistic predictor may use a function that is selected based on the type of the phenotype (e.g., binary, multi-state, or continuous). The probabilistic predictor may use genetic and/or epigenetic information. The probabilistic predictor may be trained on a portion of the data in conjunction with predicting phenotypes in another portion of the data. The probabilistic predictor may be used for various analyses including genome-wide association analysis and gene-set enrichment analysis.

20 Claims, 3 Drawing Sheets

PREDICTING PHENOTYPES USING A PROBABILISTIC PREDICTOR

BACKGROUND

Early genome-wide association studies (GWAS) focused on the association between one or a small number of single-nucleotide polymorphisms (SNPs) and a phenotype. Such studies were likely to miss associations where a large number of SNPs have a mild influence on the phenotype. Researchers have begun to look for associations based on sets of SNPs corresponding to pre-defined or learned gene sets. Finding a robust aggregation function that that quantifies the relationship between a set of SNPs and a phenotype has been elusive.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

Briefly, aspects of the subject matter described herein relate to predicting phenotypes. In aspects, a probabilistic predictor is used to summarize a relationship between a set of biological predictors and a phenotype. The probabilistic predictor may use a function that is selected based on the type of the phenotype (e.g., binary, multi-state, or continuous). The probabilistic predictor may use genetic and/or epigenetic information. The probabilistic predictor may be trained on a portion of the data in conjunction with predicting phenotypes in another portion of the data. The probabilistic predictor may be used for various analyses including genome-wide association analysis and gene-set enrichment analysis.

This Summary is provided to briefly identify some aspects of the subject matter that is further described below in the Detailed Description. This Summary is not intended to identify key or essential features of the claimed subject matter, nor is it intended to be used to limit the scope of the claimed subject matter.

The phrase "subject matter described herein" refers to subject matter described in the Detailed Description unless the context clearly indicates otherwise. The term "aspects" is to be read as "at least one aspect." Identifying aspects of the subject matter described in the Detailed Description is not intended to identify key or essential features of the claimed subject matter.

The aspects described above and other aspects of the subject matter described herein are illustrated by way of example and not limited in the accompanying figures in which like reference numerals indicate similar elements and in which:

DETAILED DESCRIPTION

Definitions

As used herein, the term "includes" and its variants are to be read as open-ended terms that mean "includes, but is not limited to." The term "or" is to be read as "and/or" unless the context clearly dictates otherwise. The term "based on" is to be read as "based at least in part on." The terms "one embodiment" and "an embodiment" are to be read as "at least one embodiment." The term "another embodiment" is to be read as "at least one other embodiment." Other definitions, explicit and implicit, may be included below.

Exemplary Operating Environment

Figure 1:
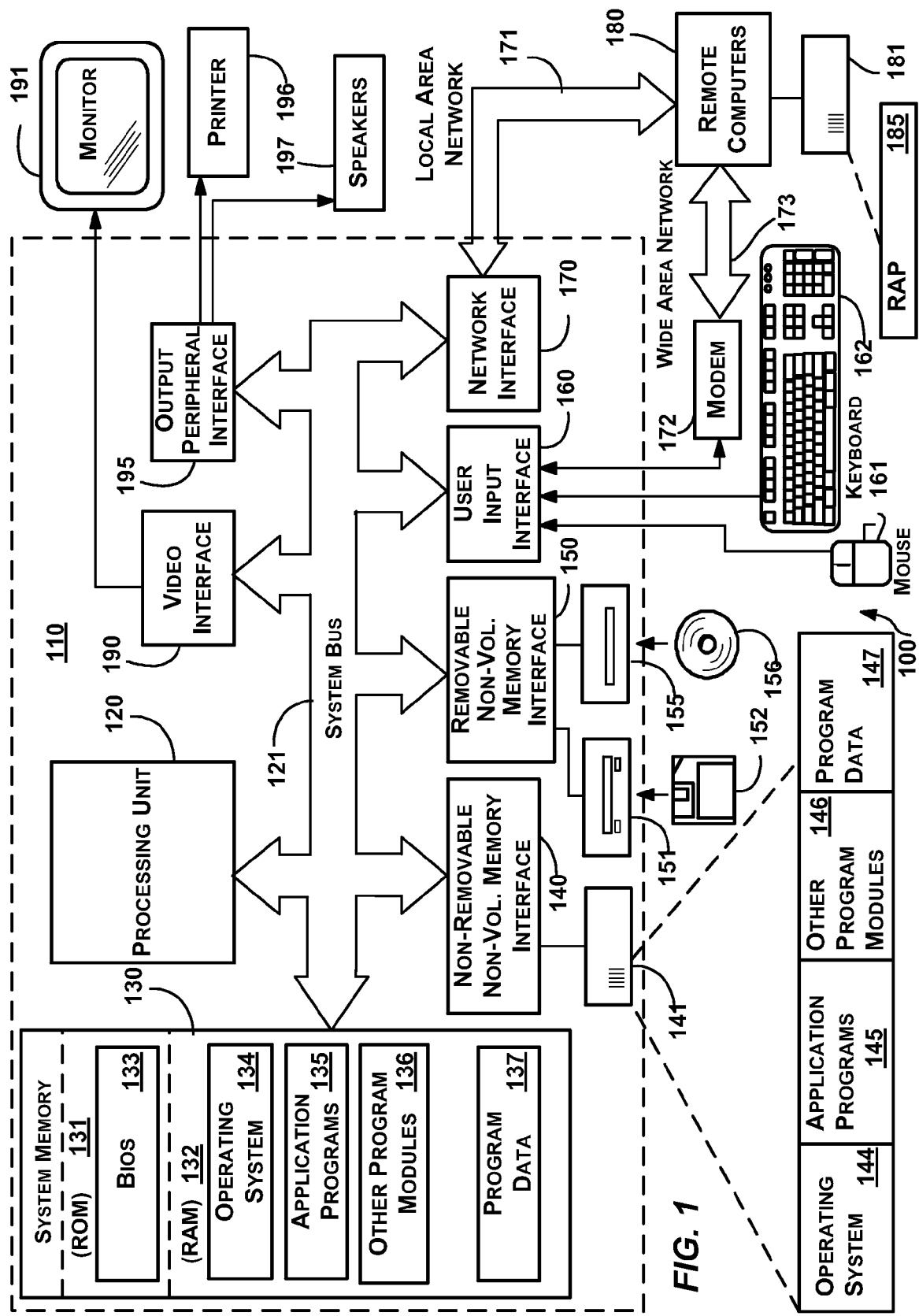
FIG. 1 is a block diagram representing an exemplary general-purpose computing environment into which aspects of the subject matter described herein may be incorporated.

FIG. 1 illustrates an example of a suitable computing system environment 100 on which aspects of the subject matter described herein may be implemented. The computing system environment 100 is only one example of a suitable computing environment and is not intended to suggest any limitation as to the scope of use or functionality of aspects of the subject matter described herein. Neither should the computing environment 100 be interpreted as having any dependency or requirement relating to any one or combination of components illustrated in the exemplary operating environment 100.

Aspects of the subject matter described herein are operational with numerous other general purpose or special purpose computing system environments or configurations. Examples of well known computing systems, environments, or configurations that may be suitable for use with aspects of the subject matter described herein comprise personal computers, server computers, hand-held or laptop devices, multiprocessor systems, microcontroller-based systems, set-top boxes, programmable consumer electronics, network PCs, minicomputers, mainframe computers, personal digital assistants (PDAs), gaming devices, printers, appliances including set-top, media center, or other appliances, automobile-embedded or attached computing devices, other mobile devices, distributed computing environments that include any of the above systems or devices, and the like.

Aspects of the subject matter described herein may be described in the general context of computer-executable instructions, such as program modules, being executed by a computer. Generally, program modules include routines, programs, objects, components, data structures, and so forth, which perform particular tasks or implement particular abstract data types. Aspects of the subject matter described herein may also be practiced in distributed computing environments where tasks are performed by remote processing devices that are linked through a communications network. In a distributed computing environment, program modules may be located in both local and remote computer storage media including memory storage devices.

With reference to FIG. 1, an exemplary system for implementing aspects of the subject matter described herein includes a general-purpose computing device in the form of a computer 110. A computer may include any electronic device that is capable of executing an instruction. Components of the computer 110 may include a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus also known as Mezzanine bus, Peripheral Component Interconnect Extended (PCI-X) bus, Advanced Graphics Port (AGP), and PCI express (PCIe).

The computer 110 typically includes a variety of computer-readable media. Computer-readable media can be any available media that can be accessed by the computer 110 and includes both volatile and nonvolatile media, and removable and non-removable media. By way of example, and not limitation, computer-readable media may comprise computer storage media and communication media.

Computer storage media includes both volatile and nonvolatile, removable and non-removable media implemented in any method or technology for storage of information such as computer-readable instructions, data structures, program modules, or other data. Computer storage media includes RAM, ROM, EEPROM, flash memory or other memory technology, CD-ROM, digital versatile discs (DVDs) or other optical disk storage, magnetic cassettes, magnetic tape, magnetic disk storage or other magnetic storage devices, or any other medium which can be used to store the desired information and which can be accessed by the computer 110.

Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 141 that reads from or writes to non-removable, nonvolatile magnetic media, a magnetic disk drive 151 that reads from or writes to a removable, nonvolatile magnetic disk 152, and an optical disc drive 155 that reads from or writes to a removable, nonvolatile optical disc 156 such as a CD ROM or other optical media. Other removable/non-removable, volatile/nonvolatile computer storage media that can be used in the exemplary operating environment include magnetic tape cassettes, flash memory cards, digital versatile discs, other optical discs, digital video tape, solid state RAM, solid state ROM, and the like. The hard disk drive 141 is typically connected to the system bus through a non-removable memory interface such as interface 140, and magnetic disk drive 151 and optical disc drive 155 are typically connected to the system bus by a removable memory interface, such as interface 150.

The drives and their associated computer storage media, discussed above and illustrated in FIG. 1, provide storage of computer-readable instructions, data structures, program modules, and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data are given different numbers herein to illustrate that, at a minimum, they are different copies.

A user may enter commands and information into the computer 20 through input devices such as a keyboard and pointing device 161, commonly referred to as a mouse, trackball, or touch pad. Other input devices (not shown) may include a microphone, joystick, game pad, satellite dish, scanner, a touch-sensitive screen, a writing tablet, or the like. These and other input devices are often connected to the processing unit 120 through a user input interface 160 that is coupled to the system bus, but may be connected by other interface and bus structures, such as a parallel port, game port or a universal serial bus (USB).

A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 195.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets, and the Internet.

When used in a LAN networking environment, the computer 110 is connected to the LAN 171 through a network interface or adapter 170. When used in a WAN networking environment, the computer 110 may include a modem 172 or other means for establishing communications over the WAN 173, such as the Internet. The modem 172, which may be internal or external, may be connected to the system bus 121 via the user input interface 160 or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are exemplary and other means of establishing a communications link between the computers may be used.

Probabilistic Predictor and Phenotypes

As mentioned previously, creating a robust aggregation function that quantifies the relationship between a set of SNPs or other biological predictors and a phenotype has been elusive. Biological predictors may include genetic predictors and epigenetic predictors. Genetic predictors include those predictors that are encoded in DNA whether found in the nucleus of a cell or otherwise. For example, a genetic predictor may include a DNA fragment.

Epigenetic predictors include those predictors that are not encoded in DNA and yet are inherited. Epigenetic predictors may, for example, include chemicals found in cells that control whether certain DNA fragments are expressed or not.

A phenotype is a characteristic of an organism. A phenotype may be binary (e.g., present or not present), multi-state (e.g., existing in one of several discrete states), or continuous. For example, a phenotype may include a good or bad reaction to a drug, susceptibility to a disease, height, weight, eye color, or any of number of other characteristics of an organism.

In humans and other organisms, there are many biological predictors that may be related to a phenotype. A probabilistic predictor (described in more detail below) may be used to summarize the relationship between a set of biological predictors and given phenotype.

Given a binary phenotype, a probabilistic predictor is a component that determines the likelihood that a phenotype will exist in the presence of one or more biological predictors. For example, in binary phenotypes, the probabilistic predictor may use a statistical test known as L1-regularized logistic regression.

Given a multi-state phenotype, the probabilistic predictor may use any function that provides a summary of the relationship between the set of biological predictors and the phenotype. As one example, the probabilistic predictor may use an L1-regularized softmax to summarize the relationship between the set of biological predictors and a phenotype. Other machine learning functions may also be used for this purpose without departing from the spirit or scope of aspects of the subject matter described herein.

Given a continuous phenotype, the probabilistic predictor may use a function suited for continuous phenotypes. As one example, the probabilistic predictor may use a statistical test known as L1-regularized linear regression.

Given biological predictors and phenotype data from a collection of individuals, data from a portion of the individuals may be used to train (e.g., via machine learning techniques, neural networks, other algorithms, and the like) a probabilistic predictor that predicts the phenotype based on just the biological predictors in the given set. This trained probabilistic predictor may then be applied to the data from another portion to yield a probability distribution (sometimes referred to as predictive probabilities or predictive distribution) over the phenotype for each individual.

In one embodiment, the portion used for training may be one half of the data while in other embodiments, the portion used for training may be a portion other than one half. In another embodiment, the portion used for training may be greater than or less than one half of the data. In one embodiment, the probabilistic predictor may be trained on one portion of the data and applied to a different portion of the data. In another embodiment, the probabilistic predictor may be trained on one portion of the data and applied to another portion of data that includes all or a portion of the trained-on data. For example, a trained-on portion and an applied-to portion may be overlapping.

Using the probability distribution, an aspect of this distribution (e.g., the mean of the distribution, probability of a particular discrete value, or other aspect) and the actual phenotype observations may be tested for using standard methods to obtain a p-value for the set of biological predictors. These tests may involve using statistical significance between an aspect of the distribution and an actual phenotype observation. A result is statistically significant if it is unlikely to have occurred by chance.

For example, when the phenotype is binary, a test such as Mann-Whitney may be performed for an association between the probability of having the phenotype and actually having the phenotype. When the phenotype is continuous, a test such as Spearman correlation may be performed for an association between the mean of the predictive distribution and the outcome.

In some studies it may be desired to summarize the relationship between DNA and a given phenotype. In particular, it may be desired to find any relationship between given SNPs (single nucleotide polymorphisms) associated with a metabolic pathway and the phenotype. A study that attempts to find a relationship between SNPs in DNA and a phenotype is sometimes referred to as a genome-wide association study (GWAS).

The techniques outlined herein may, however, also be applied to gene-set enrichment analysis (GSEA). In GSEA, gene expressions rather than SNPs are used to predict phenotype (including experimental conditions). Gene expression includes, for example, levels of particular mRNA or other chemicals that may be found in a cell. To apply the techniques herein, data regarding the level of biological predictors (e.g., mRNA) may be provided to a probabilistic predictor together with a phenotype to determine a relationship between the biological predictors and the phenotype.

Figure 2:
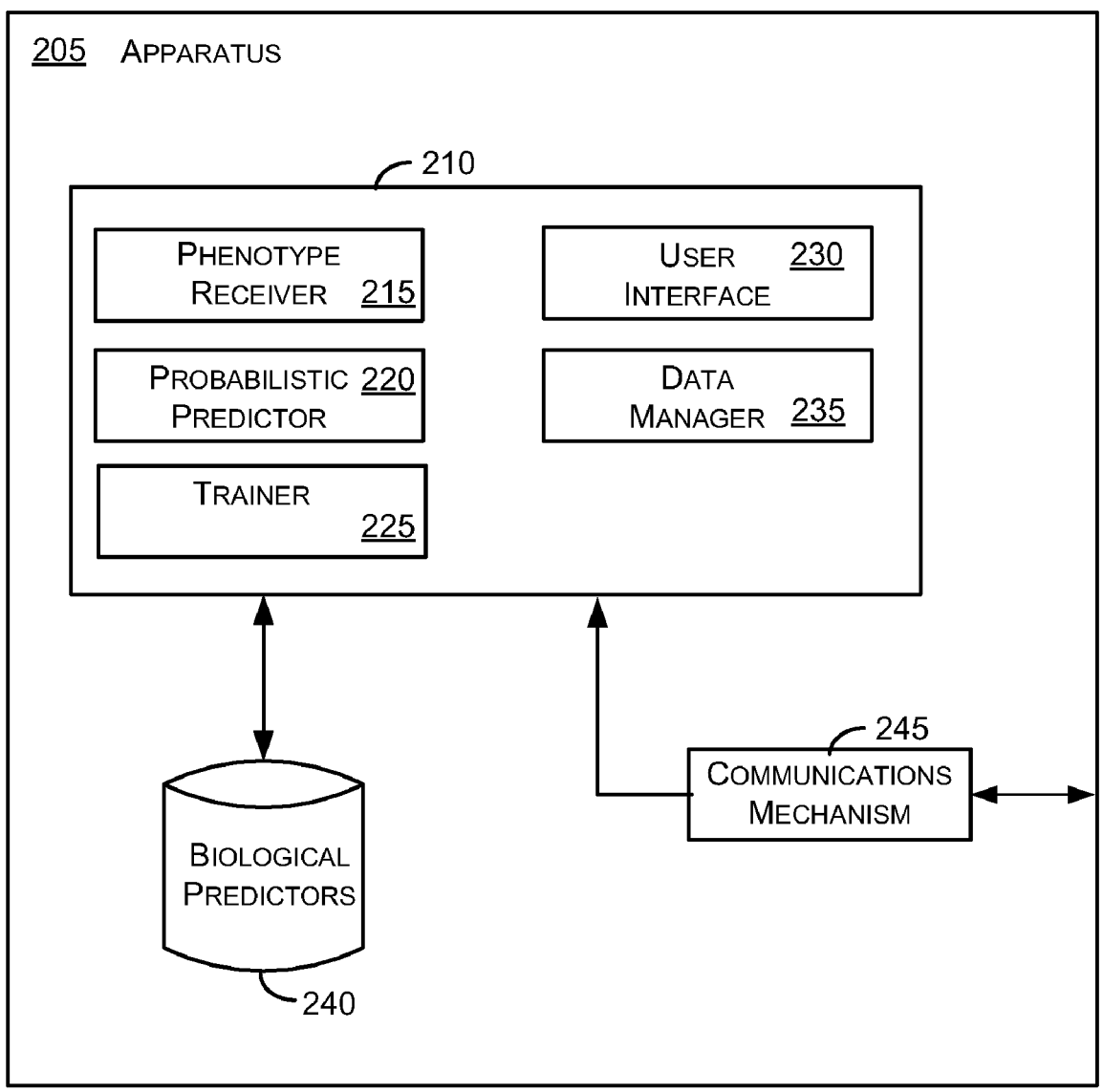
FIG. 2 is a block diagram that represents an apparatus configured in accordance with aspects of the subject matter described herein.

FIG. 2 is a block diagram that represents an apparatus configured in accordance with aspects of the subject matter described herein. The components illustrated in FIG. 2 are exemplary and are not meant to be all-inclusive of components that may be needed or included. In other embodiments, the components and/or functions described in conjunction with FIG. 2 may be included in other components (shown or not shown) or placed in subcomponents without departing from the spirit or scope of aspects of the subject matter described herein. In some embodiments, the components and/or functions described in conjunction with FIG. 2 may be distributed across multiple devices.

Turning to FIG. 2, the apparatus 205 may include predicting components 210, a store 240, a communications mechanism 245, and other components (not shown). The apparatus 205 may comprise or reside on one or more computing devices. Such devices may include, for example, personal computers, server computers, hand-held or laptop devices, multiprocessor systems, microcontroller-based systems, set-top boxes, programmable consumer electronics, network PCs, minicomputers, mainframe computers, cell phones, personal digital assistants (PDAs), gaming devices, printers, appliances including set-top, media center, or other appliances, automobile-embedded or attached computing devices, other mobile devices, distributed computing environments that include any of the above systems or devices, and the like. An exemplary device that may be configured to act as the apparatus 205 comprises the computer 110 of FIG. 1.

The predicting components 210 may include a phenotype receiver 215, a probabilistic predictor 220, a trainer 225, a user interface 230, a data manager 235, and other components (not shown). As used herein, the term component is to be read to include all or a portion of a device, a collection of one or more software modules, some combination of one or more software modules and one or more devices, and the like.

The communications mechanism 245 allows the apparatus 205 to communicate with other entities. The communications mechanism 245 may be a network interface or adapter 170, modem 172, or any other mechanism for establishing communications as described in conjunction with FIG. 1.

The store 240 is any storage media capable of storing data associated with biological predictors and phenotypes. The store 240 may be used for input data, output data, and computations, as needed. The store 240 may comprise a file system, database, volatile memory such as RAM, other storage, some combination of the above, and the like and may be distributed across multiple devices. The store 240 may be external, internal, or include components that are both internal and external to the apparatus 205.

The phenotype receiver 215 is operable to obtain a phenotype. This phenotype may be then be used by the probabilistic predictor 220 to determine the relationship between the phenotype and a set of one or more biological predictors. The phenotype receiver 215 may utilize the user interface 230 to obtain the phenotype from a user or may use the data manager 235 to obtain the phenotype from the store 240.

The probabilistic predictor 220 is operable to summarize the relationship between the set of biological predictors and the phenotype. The probabilistic predictor 220 may summarize the relationship as a value, in a table that has multiple values, as a graph, bar chart, pie chart, or some other chart, in some other way, and the like. The probabilistic predictor 220 may use various functions/tests including, for example, an L1-regularized logistic regression function, the Mann-Whitney test, Spearman's rank correlation, other tests, and the like to assist in summarizing the relationship.

The trainer 225 may operate to train the probabilistic predictor 220 on a portion of the data. As mentioned previously, various machine learning algorithms may be used to do this.

The user interface 230 is operable to interact with users. The user interface 230 may receive indications of biological predictors and phenotypes and may display information that summarizes the relationship between a set of biological predictors and a phenotype.

The data manager 235 provides access to the store 240. Access as used herein may include reading data, writing data, deleting data, updating data, a combination including two or more of the above, and the like. Where the data is organized in files, the data manager 235 may comprise components that are operable to access the files.

Where the data is organized as a database, the data manager 235 may comprise a database management system (DBMS). A DBMS may comprise one or more programs that control organization, storage, management, and retrieval of data of a database. A DBMS may receive requests to access data in the store 240 and may perform the operations needed to provide this access.

Figure 3:
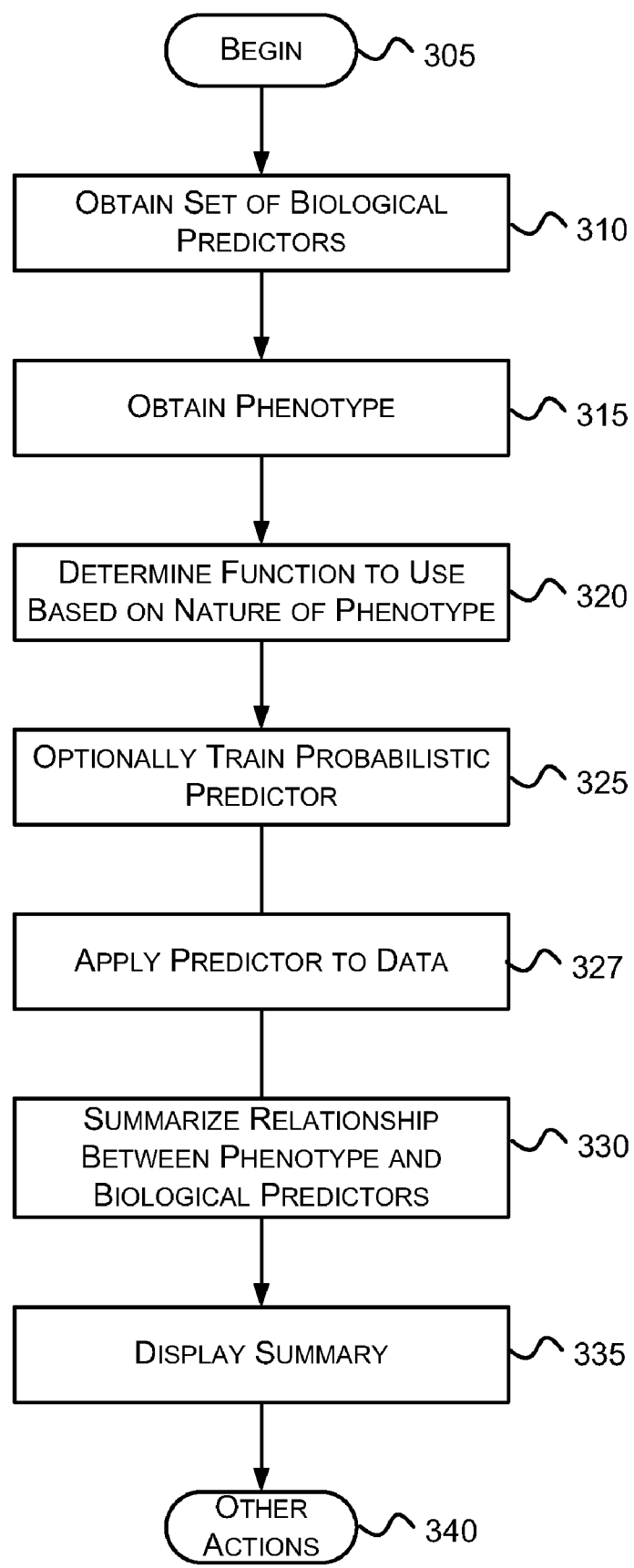
FIG. 3 is a flow diagram that generally represents actions that may occur in accordance with aspects of the subject matter described herein.

FIG. 3 is a flow diagram that generally represents actions that may occur in accordance with aspects of the subject matter described herein. For simplicity of explanation, the methodology described in conjunction with FIG. 3 is depicted and described as a series of acts. It is to be understood and appreciated that aspects of the subject matter described herein are not limited by the acts illustrated and/or by the order of acts. In one embodiment, the acts occur in an order as described below. In other embodiments, however, the acts may occur in parallel, in another order, and/or with other acts not presented and described herein. Furthermore, not all illustrated acts may be required to implement the methodology in accordance with aspects of the subject matter described herein. In addition, those skilled in the art will understand and appreciate that the methodology could alternatively be represented as a series of interrelated states via a state diagram or as events.

Turning to FIG. 3, at block 305, the actions begin. For example, referring to FIG. 2, a user may indicate via the user interface 230 a desire to find a relationship between a set of biological predictors and a phenotype.

At block 310, data regarding a set of biological predictors is obtained. For example, referring to FIG. 2, the data manager 235 may be used to access the data from the store 240. This data may include, for example, DNA fragments, genes or portions thereof, levels of molecules expressed in a cell, epigenetic data, or other biological predictors.

At block 315, a phenotype is obtained. For example, referring to FIG. 2, the user interface 230 or the data manager 235 may obtain a phenotype for use in the probabilistic predictor 220.

At block 320, a function may be selected to use with the probabilistic predictor. The selection may be based on the nature (e.g., binary, multi-state, continuous) of the phenotype. For example, if the phenotype is height (i.e., a continuous phenotype), a function corresponding to the Spearman correlation may be selected.

At block 325, the probabilistic predictor may be trained using a portion of the data. For example, referring to FIG. 2, the trainer 225 may train the probabilistic predictor 220 using a portion of the data regarding the set of biological predictors obtained at block 310.

At block 327, the probabilistic predictor may be applied to a portion of the data. For example, referring to FIG. 2, the probabilistic predictor 220 may be applied to a portion of the data to produce predictive probabilities of the phenotype for the portion of the data.

At block 330, the relationship between the biological predictors and the phenotype is summarized. For example, referring to FIG. 2, the probabilistic predictor may determine a value or set of values to assign to the relationship.

At block 335, the summary is displayed. For example, referring to FIG. 2, the user interface 230 may be used to display the summary on a monitor (not shown).

At block 340, other actions, if any, may be performed.

As can be seen from the foregoing detailed description, aspects have been described related to predicting phenotypes. While aspects of the subject matter described herein are susceptible to various modifications and alternative constructions, certain illustrated embodiments thereof are shown in the drawings and have been described above in detail. It should be understood, however, that there is no intention to limit aspects of the claimed subject matter to the specific forms disclosed, but on the contrary, the intention is to cover all modifications, alternative constructions, and equivalents falling within the spirit and scope of various aspects of the subject matter described herein.

What is claimed is:

1. A method for determining a relationship between biological predictors and a phenotype, the method implemented at least in part by a computer, the method comprising:

obtaining data regarding a set of biological predictors, the set of biological predictors including a first portion comprising labeled training wherein biological predictors in the first portion have labels to indicate corresponding phenotypes, the set of biological predictors including a second portion;

obtaining an indication of the phenotype;

training a probabilistic predictor using the labeled training data to predict the phenotype based on the set of biological predictors, the probabilistic predictor comprising a statistical model of the set of biological predictors that, given input biological predictors and input phenotypes, computes predictive probabilities of the input biological predictors in relation to the input phenotypes;

applying the trained probabilistic predictor to the second portion of the data to compute predictive probabilities of the phenotype for the second portion of the data, the predictive probabilities comprising probabilities that the biological predictors in the second portion are predictive of the phenotype; and using statistical significance between an aspect of the predictive probabilities and actual phenotype observations to summarize the relationship between the set of biological predictors and the phenotype.

2. The method of claim 1, wherein applying the probabilistic predictor comprises using the probabilistic predictor in a genome-wide association analysis.

3. The method of claim 1, wherein applying the probabilistic predictor comprises using the probabilistic predictor in a gene-set enrichment analysis.

4. The method of claim 1, wherein the biological predictors comprise genetic predictors.

5. The method of claim 4, wherein the genetic predictors comprise single-nucleotide polymorphisms.

6. The method of claim 1, wherein the biological predictors comprise epigenetic predictors.

7. The method of claim 1, wherein applying the probabilistic predictor comprises using an L1-regularized function.

8. The method of claim 1, wherein applying the probabilistic predictor comprises using a statistical test known as the Mann-Whitney test.

9. The method of claim 1, wherein applying the probabilistic predictor comprises using a statistical test according to Spearman correlation.

10. The method of claim 1, wherein the aspect comprises a mean of a distribution or a probability of a discrete value.

11. The method of claim 1, wherein obtaining data regarding a set of biological predictors comprises obtaining data regarding a metabolic pathway associated with the set of biological predictors.

12. The method of claim 1, further comprising displaying a value indicative of the relationship.

13. In a computing environment, an apparatus for determining a relationship between biological predictors and a target phenotype, the apparatus comprising:

a store that includes data regarding a set of biological predictors, the set of biological predictors including a first portion comprising labeled training wherein biological predictors in the first portion have labels to indicate corresponding phenotypes, the set of biological predictors including a second portion;

a phenotype receiver operable to obtain the target phenotype;

a probabilistic predictor operable to summarize the relationship between the second portion of the set of biological predictors and the target phenotype; and a trainer operable to train the probabilistic predictor on a portion of the data using the labeled training data on the set of biological predictors, the probabilistic predictor comprising a statistical model of the set of biological predictors that, given input biological predictors and input phenotypes, computes predictive probabilities of the input biological predictors in relation to the input phenotypes.

14. The apparatus of claim 13, wherein the probabilistic predictor is operable to use an L1-regularized logistic regression function to assist in summarizing the relationship.

15. The apparatus of claim 13, wherein the probabilistic predictor is operable to use a function that implements the Mann-Whitney test to assist in summarizing the relationship.

16. The apparatus of claim 13, wherein the probabilistic predictor uses a statistical test according to Spearman correlation to assist in summarizing the relationship.

17. The apparatus of claim 13, further comprising a user interface operable to receive indications of biological predictors and phenotypes.

18. The apparatus of claim 13, wherein the biological predictors comprise genetic predictors.

19. The apparatus of claim 13, wherein the biological predictors comprise epigenetic predictors.

20. A computer storage medium having computer-executable instructions for determining a relationship between biological predictors and a phenotype, the computer-executable instructions when executed performing actions, comprising:

obtaining data regarding a set of biological predictors that are genetic and/or epigenetic in nature, the biological predictors related to a metabolic pathway, the set of biological predictors including a first portion comprising labeled training wherein biological predictors in the first portion have labels to indicate corresponding phenotypes, the set of biological predictors including a second portion;

obtaining an indication of the phenotype, the phenotype comprising a characteristic of an organism, the phenotype having a nature of binary, multi-state, or continuous;

selecting a function to use for a probabilistic predictor based on the nature of the phenotype, the function corresponding to one of a L1-regularized function, Mann-Whitney test, and Spearman correlation;

training the probabilistic predictor based on a labeled portion of the data, the labeled portion comprising biological predictors having labels indicating phenotypes associated therewith; and using the probabilistic predictor to summarize the relationship between the set of biological predictors and the phenotype.

* * * * *